United States Patent [19]
Steinman

[11] 4,081,549
[45] Mar. 28, 1978

[54] ANTIMICROBIAL BENZOTHIOPHENES

[75] Inventor: Martin Steinman, Livingston, N.J.

[73] Assignee: Schering Corporation, Kenilworth, N.J.

[21] Appl. No.: 758,739

[22] Filed: Jan. 12, 1977

Related U.S. Application Data

[60] Division of Ser. No. 640,291, Dec. 12, 1975, Pat. No. 4,018,893, which is a continuation-in-part of Ser. No. 473,625, May 28, 1974, Pat. No. 3,944,672.

[30] Foreign Application Priority Data

May 22, 1975 United Kingdom ............... 22371/75

[51] Int. Cl.$^2$ ...................... A61K 31/38; A61K 31/34
[52] U.S. Cl. ..................................... 424/275; 424/285
[58] Field of Search ......................................... 424/275

[56] References Cited
PUBLICATIONS

Derwent Farmdoc No. 11406T, Abstracting JA-72052-53-R, published 2-15-72.
Derwent Basic No. 9956, Fr 1,343,074, published 11-15-63.

*Primary Examiner*—Jerome D. Goldberg
*Attorney, Agent, or Firm*—Bruce M. Eisen; Stephen B. Coan

[57] ABSTRACT

Disclosed herein are 2-aminoalkyl-3-aryl-benzothiophenes and benzofurans useful as antimicrobial agents.

4 Claims, No Drawings

ANTIMICROBIAL BENZOTHIOPHENES

This is a division, of application Ser. No. 640,291 now U.S. Pat. No. 4,018,893 filed 12/12/75, which in turn is a continuation-in-part of Application Ser. No. 473,625 filed 5/28/74, now U.S. Pat. No. 3,944,672.

This invention relates to antimicrobial compounds and compositions containing them, to processes for their preparation, and to their use as antimicrobial agents.

The antimicrobial compounds of the invention are 2-aminoalkyl-3-phenyl- or 3-benzyl-benzo[b]furans or benzo-[b]thiophenes of the formula

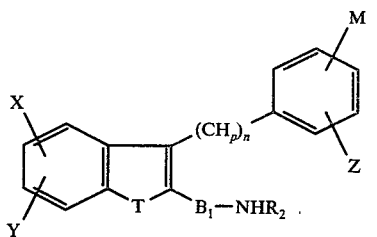

wherein $n$ is 0 or 1;

T is an oxygen or sulfur atom;

X is a halogen atom or a nitro or trifluoromethyl group;

Y is a hydrogen or halogen atom or a methyl or trifluoromethyl group;

M is a hydrogen or halogen atom or a methyl or trifluoromethyl group;

Z is a hydrogen or halogen atom or a nitro, methyl or trifluoromethyl group;

$R_1$ is a carbonyl or an alkylene group having 1 to 3 carbon atoms with the proviso that when $R_2$ is hydrogen, $R_1$ is said alkylene group. $R_1$ is preferably CHR wherein R is a hydrogen atom or a methyl group.

$R_2$ is a hydrogen atom or an aminoalkyl group having 2 or 3 carbon atoms; $R_2$ is preferably hydrogen. $R_2$ aminoalkyl groups include β-aminoethyl, β-aminopropyl, γ-aminopropyl and α-methyl-β-aminoethyl.

and the acid addition salts, especially the non-toxic acid addition salts, thereof.

The group X is preferably fixed at the 5-position. In a preferred embodiment X is chlorine, especially 5-chloro.

The term "halogen" herein comprises fluorine, chlorine, bromine and iodine.

M is preferably a 2-halogen atom, especially 2-fluorine or 2-chlorine. The M,Z-phenyl group is preferably 2-fluorophenyl, 2,6-difluorophenyl, or 2,4-dichlorophenyl.

$n$ is preferably 0.

When X is a nitro group, at least one of Y, M and Z is preferably a halogen atom or a trifluoromethyl group.

In a particularly useful group of anti-microbial 2-aminoalkyl-3-phenyl-benzo[b]furans and benzo[b]thiophenes within formula I, X is a halogen atom or a trifluoromethyl group, Y is a hydrogen, iodine, bromine or chlorine atom, $R_1$ is a methylene or ethylene group, and one of M and Z is a hydrogen atom or a 2-fluorine or 2-chlorine atom and the other is a hydrogen or halogen atom or a nitro or trifluoromethyl group. It is particularly preferred for the M,Z-phenyl group to be phenyl, 2-fluorophenyl, 2,6-difluorophenyl, or 2,4-dichlorophenyl. Particularly preferred compounds of formula I include:

2-Aminomethyl-5-chloro-7-iodo-3-phenylbenzo[b]furan;
2-Aminomethyl-5-chloro-3-phenylbenzo[b]furan; and
2-Aminomethyl-5-chloro-3-(2,4-dichlorophenyl)benzo[b]furan;
2-Aminomethyl-5-bromo-3-phenylbenzo[b]thiophene.

These compounds can be particularly conveniently used as their hydrochlorides.

Other exemplary compounds of formula I include:
2-Aminomethyl-3-(2,4-dichlorophenyl)-5-trifluoromethylbenzo[b]thiophene;
2-Aminomethyl-5-chloro-3-(2-fluorophenyl)benzo[b]thiophene;
2-Aminomethyl-5,6-dichloro-3-(2-fluorobenzyl)benzo[b]thiophene;
2-Aminomethyl-6-bromo-3-(2,6-dichlorobenzyl)benzo[b]furan;
2-Aminomethyl-5,6-dichloro-3-(2,4-dichlorophenyl)benzo[b]thiophene;
2-Aminoethyl-5-iodo-3-(2,4-dichlorophenyl)benzo[b]thiophene;
2-Aminomethyl-3-(2-chloro-6-methyl-benzyl)benzo[b]thiophene;
2-Aminomethyl-5-chloro-3-(2,4-dimethylphenyl)-benzo[b]furan;
2-Aminomethyl-5-chloro-3-(2-chloro-6-trifluoromethylbenzyl)benzo[b]furan;
2-[N-(2-Aminoethyl)aminoethyl]-5-nitro-3-(2,4-di-trifluoromethylphenyl)benzo[b]furan;
2-Aminomethyl-5-chloro-3-(2,6-difluorophenyl)benzo[b]furan;
2-Aminomethyl-6-bromo-5-chloro-3-phenylbenzo[b]thiophene;
2-Aminomethyl-5-chloro-3-(2,4-dichlorobenzyl)benzo[b]furan;
2-(1-Aminoethyl)-6-bromo-5-chloro-3-benzylbenzo[b]thiophene;
2-Aminomethyl-5,7-dichloro-3-(2,4-dichlorophenyl)benzo[b]furan;
2-Aminomethyl-5,7-dichloro-3-(2,4-dichlorophenyl)benzo[b]thiophene;
5-Chloro-3-(3,4-dichlorophenyl)-benzo[b]furan-2-(N-2-aminoethyl) carboxamide;
5-Chloro-3-(2,4-dichlorophenyl)-6-nitrobenzo[b]furan-2-(N-3-aminopropyl)carboxamide;
2-Aminomethyl-6-chloro-5-fluoro-3-(4-nitrophenyl)benzo-[b]furan;
2-Aminomethyl-3-(2,4-dichlorophenyl)-5-iodobenzo[b]furan;
2-Aminomethyl-3-(2,4-dichlorophenyl)-5-trifluoromethylbenzo[b]furan;
2-[N-(2-Aminoethyl)aminomethyl]-6-chloro-3-(2,4-dichlorophenyl)benzo[b]thiophene;
2-Aminomethyl-5-chloro-3-(2,4-dichlorophenyl)-6-methylbenzo[b]thiophene;
2-Aminomethyl-3-(2-chloro-6-methyl-phenyl)-5-trifluoromethylbenzo[b]furan;
2-Aminomethyl-5-chloro-3-(3,4-dimethylphenyl)benzo[b]furan;
2-(2-Aminoethyl)-5,7-dichloro-3-(2-fluorophenyl)benzo[b]furan;
2-(3-Aminopropyl)-5,7-dichloro-3-(2-fluorophenyl)benzo-[b]furan; and
2-(2-Aminoethyl)-5,7-dichloro-3-benzylbenzo[b]furan.

The acid addition salts can sometimes be used more conveniently than the benzo[b]furans and benzo[b]thiophenes themselves; for example, because the salts have more convenient physical properties such as crystalline form or solubility, or because the salts are more readily purified by recrystallization, than the benzo[b]furans or benzo[b]-thiophenes. When the salts are used in food or medicine, the anion must, of course, be substantially non-toxic at the concentration or dosage used; when the salts are used in technical fields such as the preservation of paper, leather, or photographic goods, the anion need not necessarily be non-toxic.

Preferred salts thus include the hydrochlorides, sulfates, nitrates, phosphates, acetates and succinates of the compounds of the formula I, and also those salts wherein the anion itself imparts antimicrobial activity, e.g., where the acid is a phenol, in particular hexylresorcinol.

The compounds of the formula I and their acid addition salts can be prepared by standard methods that are known for the preparation of benzo[b]furans or benzo[b]thiophenes or for modification of substituents in an aromatic nucleus. These modifications may for example be transformation of the 2-substituent into a 2-$R_1$.$NHR^2$ substituent, or removal of an N-blocking or N-protecting group from the 2-$R_1$.$NHR^2$ group ($R_1$ and $R_2$ being as hereinbefore defined).

By way of example, the 2-aminoalkyl-3-phenyl-benzo[b]-thiophenes can be prepared from methyl 3-phenyl-benzo[b]-thiophene-2-carboxylate, known from Krubsack and Higa in *Tetrahedron Letters* No. 47, page 4823 (1972), by standard methods. The 2-aminoalkyl-3-phenyl-benzo[b]furans can be prepared from the 2-cyano-3-phenyl-benzo[b]furans, known from standard methods.

The following examples illustrate the preparation of compounds of the formula I:

EXAMPLE 1

2-Aminomethyl-5-bromo-3-phenylbenzo[b]-thiophene hydrochloride

Step A: Methyl 5-bromo-3-phenylbenzo[b]thiophene-2-carboxylate

Add 29.3 g. of bromine (10 ml.; 0.37 mole) to 8.0 g. (0.03 mole) of methyl 3-phenylbenzo b thiophene-2-carboxylate in 100 ml. of acetic acid and stir the mixture overnight at room temperature. Add a saturated solution of sodium bisulfite. Decant the supernatant; wash the oil with water and triturate it with methanol. Recrystallize the product from methanol to obtain the title compound; m.p. 125°-126°.

Step B: 5-Bromo-3-phenylbenzo[b]thiophene-2-carboxylic acid

Heat 3 g. of methyl 5-bromo-3-phenyl-benzo[b]-thiophene-2-carboxylate in a mixture of 50 ml. of methanol and 30 ml. of 10% sodium hydroxide under reflux for one hour. Add concentrated hydrochloric acid to yield the title compound as a precipitate. Recrystallize it from benzene; m.p. 265°-266°.

Step C: 5-Bromo-3-phenylbenzo[b]thiophene-2-carboxamide

Reflux 2.8 g. of 5-bromo-3-phenylbenzo[b]thiophene-2-carboxylic acid (0.0084 mole) and 10 ml. of thionyl chloride in 15 ml. of dry tetrahydrofuran for one hour; evaporate to dryness, add 50 ml. of tetrahydrofuran twice and evaporate each time to dryness. Dissolve the resulting solid in 70 ml. of tetrahydrofuran, cool to about 10° and add with stirring 10 ml. of concentrated ammonia. The title compound is obtained as a white solid; m.p. 201°-202°.

Step D: 5-Bromo-2-cyano-3-phenylbenzo[b]thiophene

Reflux 2.1 g. 5-bromo-3-phenylbenzo[b]thiophene-2-carboxamide (0.0063 mole) together with 10 ml. of phosphorus oxychloride for 1½ hours and then carefully pour into ice water. Filter off the white precipitate and dry it; recrystallize it from methanol to obtain the title compound; m.p. 145°-146°.

Step E: 2-Aminomethyl-5-bromo-3-phenylbenzo[b]thiophene hydrochloride

Treat 1.4 g. of 5-bromo-2-cyano-3-phenylbenzo[b]thiophene (0.0045 mole) in 40 ml. of tetrahydrofuran with 10 ml. of 1 molar diborane in tetrahydrofuran. Reflux the solution for 1½ hours. Slowly add 10 ml. of 5% hydrochloric acid. Heat the mixture for ½ hour, cool and add sufficient sodium hydroxide solution to basicity. Extract the solution with ether and wash twice with water. Dry the ether layer ($MgSO_4$), filter and mix with 50 ml. of ether saturated with hydrogen chloride. Dry the precipitate to obtain the title compound; m.p. over 225° (decomp).

EXAMPLE 2

2-Aminomethyl-5-chloro-3-phenylbenzo[b]furan hydrochloride

Treat 2.0 g. of 2-cyano-5-chloro-3-phenylbenzo[b]furan (0.008 mole) in 30 ml. of tetrahydrofuran with 18 ml. of diborane in tetrahydrofuran (1 M solution) and reflux for 2 hours. Cool, add 10 ml. of 10% hydrochloric acid and reflux for ½ hour. Evaporate the solution to dryness and dissolve the residue in 50 ml. of ethanol. Add 30 ml. of ethanol saturated with hydrogen chloride. Dry the precipitate obtained to yield the title compound; m.p. 254°-256°.

EXAMPLE 3

2-Aminomethyl-5-chloro-7-iodo-3-phenyl benzo[b]furan

Step A: 5-Chloro-2-Hydroxy-3-Iodobenzophenone

Add 5-chloro-2-hydroxybenzophenone (23.2 g., 0.1 mole) to acetic acid (150 ml.(and sodium acetate (9.3 g., 0.11 mole). Treat the mixture with iodine monochloride (16.5 g., 0.1 mole) and warm in a bath at 70°-85° for one hour. Cool and add 20 ml. of sodium bisulfite solution and then more water. After stirring for five minutes, collect and dry the title compound; m.p. 110°-111° C.

Step B: 5-Chloro-7-iodo-3-phenylbenzo[b]furan-2-carboxylic acid

Add 28 ml. (42.0 g., 0.25 mole) of ethyl bromoacetate to 58 g. (0.16 mole) of 5-chloro-2-hydroxy-3-iodobenzophenone in acetone (500 ml.) containing potassium carbonate (60 g.). Boil under reflux with stirring for two hours, and filter hot, washing the filter cake with acetone. Evaporate the combined filtrates to dryness and dissolve the oil obtained in dry ethanol (500 ml.).

After adding sodium methoxide (8.0 g.), boil under reflux, adding more dry alcohol (500 ml.) if necessary so that efficient stirring is maintained. After one half hour, add 10% sodium hydroxide (300 ml.) and boil under reflux for two more hours.

Cool the solution and neutralize with hydrochloric acid; collect and dry the precipitate. Add hot methanol (600 ml.) to this material and stir, add water and after standing for one hour collect and dry the precipitate; m.p. 274°–275° C.

Step C: 5-Chloro-7-iodo-3-phenylbenzo[b]furan-2-carboxamide

Boil under reflux 6.5 g. of 5-chloro-7-iodo-3-phenylbenzo[b]furan-2-carboxylic acid in 15 ml. of thionyl chloride. After an hour, remove the excess of thionyl chloride in vacuo.

Add 30 ml. of tetrahydrofuran to the oil, cool to 0° and add 1 ml. of liquid ammonia. After stirring for 15 minutes, filter and wash the filter cake with tetrahydrofuran. Add hexane and ether to the combined filtrates and collect and dry the crystals; m.p. 205°–206° C.

Step D: 2-Aminomethyl-5-chloro-7-iodo-3-phenylbenzo[b]furan

Add 150 ml. of a 1M solution of borane in tetrahydrofuran to 15.0 g. (0.038 mole) of 5-chloro-7-iodo-3-phenylbenzo[b]furan-2-carboxamide in 130 ml. of tetrahydrofuran and boil under reflux for 16 hours. Treat the solution with 8 ml. of 5% hydrochloric acid and reflux for 45 minutes more. Cool and make basic with sodium hydroxide solution.

Evaporate the tetrahydrofuran with a stream of nitrogen. Extract with methylene chloride, and then wash this layer with water, dry over magnesium sulfate, filter and evaporate to an oil. Dissolve this material in ether and add ether saturated with hydrogen chloride. Collect and dry the precipitate; m.p. 244°–246° C. (decomp.)

To obtain the free base treat the salt with alkali, extract with methylene chloride and recrystallize the extracted base from isopropanol; m.p. 128°–130° C. The compounds of formula I and their non-toxic acid addition salts can be used to treat diverse types of susceptible microbial infections. Furthermore, they are capable of preserving a wide variety of preparations including medical, veterinary, cosmetic and food preparations from microbial contamination; a stabilizing amount of such a compound is incorporated in the preparation in which the preservation is desired.

Susceptibility can be readily determined by standard in vivo and in vitro tests well known to the microbiologist. Genera of susceptible microorganisms include bacteria, fungi, and protozoa.

Exemplifying susceptible bacterial microorganisms are *Staphylococcus aureus, Streptococcus pyogenes* C., *Bacillus subtilis, Escherichia coli* and *Pseudomonas aeruginosa*. Susceptible fungi include *Candida albicans, Trichophyton mentagrophytes* and *Saccharomyces cerevisiae*. Susceptible protozoal pathogens include *Trychomonas vaginalis* and *Entamoeba histolytica*.

A carrier susceptible to microbial contamination preferably contains from 0.05 to 1%, especially 0.1 to 0.5%, by weight of active ingredient of the formula I or acid addition salt thereof; a concentrate for dilution to apply to a carrier susceptible to microbial contamination will normally contain from 1% up to 25% (if liquid) or up to 90% (if solid) of the compound of formula I or acid addition salt thereof, together with solvents such as water, aliphatic ketones (especially acetone) or alcohols (especially ethanol), aerosol propellants such as chlorofluoroalkanes, and stabilising, thickening, suspending, dispersing, emulsifying, surface-active, buffering and/or wetting agents.

Thus, in its function as active ingredient, the compound of the formula I or salt thereof may be used to preserve the carrier from microbial contamination; for example, the carrier may be paper, leather, photographic emulsion, canvas, cutting or other oil or rope. If the salt is non-toxic, the carrier may also be a food-stuff, food-additive or food-supplement, or a medicinal or cosmetic preparation that is liable to microbial contamination. Such medicinal or cosmetic preparations may conveniently be in fluid form, e.g., lotions, creams, ointments, solutions, suspensions or aerosol preparations.

The compounds of formula I and their non-toxic acid addition salts can themselves be used in medicine as antimicrobial agents, and thus may be formulated as pharmaceutical compositions containing at least one said compound or salt together with a pharmaceutical carrier or excipient. Such a composition may for example be in the form of shaped products, in particular dosage units, such as pills, tablets, capsules, dragees, lozenges or suppositories (especially vaginal suppositories). Alternatively, such compositions may be adapted for injection and therefore have as carrier a sterile, pyrogen-free injectable liquid. Injectable compositions will normally be in the form of dosage units; the various dosage units mentioned conveniently contain from 2 to 100 mg., preferably from 5 to 50 mg., of a compound of formula I or non-toxic acid addition salt thereof.

Compositions for oral administration, other than dosage units mentioned above, may be exemplified by powders, granulates, solutions, suspensions, elixirs or aerosols. Compositions for topical application may be exemplified by ointments, creams, lotions, solutions, suspensions, aerosols, gels, shampoos, soaps or dusting powders. The compositions may be adapted in particular as ophinalmic, otic and nasal preparations. Such compositions will normally be based upon standard carriers such as those selected from pharmaceutically acceptable polyalkylene glycols, isopropanol, gelatin, benzyl alcohol, gums, glycerol, petrolatum, perservatives, starch, sugars such as lactose, talc, magnesium stearate, aerosol propellants such as chlorofluoroalkanes, and colouring, flavoring, sweetening, thickening, suspending, dispersing, emulsifying, wetting, stabilising and buffering agents.

The composition may also be in the form of an animal feed-stock, feed-additive or feed-supplement.

Compositions in which the active ingredient is a compound of the formula I or non-toxic acid addition salt thereof preferably contain from 0.5 to 10% thereof.

A suitable parenteral dosage range of the compounds of the formula I and non-toxic acid addition salts thereof is about 2 to 10 mg./kg./day. The compounds of formula I and their non-toxic acid addition salts may be formulated into dosage forms as the sole active ingredient or used in association with other ingredients to extend the therapeutic spectrum.

The following formulations exemplify pharmaceutical compositions containing compounds of this invention; the active ingredient or preservative may of course be any compound of formula I or non-toxic acid addition salt thereof, but is preferably the compound of Example 3.

Formulation 1

| Topical Cream | Per kg. |
| --- | --- |
| Active ingredient | 10 g. –100 g. |
| Ethoxylated Cetyl/Stearyl Alcohol | 20 g. |

Formulation 1-continued

| Topical Cream | Per kg. |
| --- | --- |
| Cetyl Alcohol | 35 g. |
| Stearyl Alcohol | 35 g. |
| Petrolatum | 200 g. |
| Mineral Oil | 50 g. |
| Buffers, Sufficient | — |
| Preservatives, Sufficient | — |
| Purified Water to make | 1.0 kg. |

Add the cetyl alcohol, stearyl alcohol, ethoxylated cetyl/stearyl alcohol, petrolatum and nimeral oil to a suitable mixing vessel, heat to 80° C. to melt, and mix. Add the preservatives, buffers and active ingredient in approximately 95% of the purified water heated to 80° C. in a separate mixing vessel and mix. Add the melted wax phase to the aqueous phase and mix while cooling to about 40° C. Add sufficient purified water to make 1 kg. and mix until cool.

Formulation 2

| Topical Ointment | Per kg. |
| --- | --- |
| Active ingredient | 10 g. -100 g. |
| White Petrolatum, to make | 1.0 kg. |

Melt and heat the petrolatum to 50° C. in a suitable mixing vessel. Remove a portion of the melted petrolatum and make therewith a slurry of the active ingredient. Pass the slurry through a suitable colloid mill and mill until a uniform dispersion is obtained. Add the milled slurry to the remainder of the melted petrolatum and mix until cool.

Formulation 3

| Otic Suspension | mg/ml |
| --- | --- |
| Active ingredient | 5 -10 |
| Cetylpyridinium Chloride, NF | 0.20 |
| Glyceryl Triacetate | 880.0 |
| Polyethylene Glycol 200 q.s. ad | 1.0 ml |

Formulation 4

| Vaginal Tablets | mg/tablet | mg/tablet |
| --- | --- | --- |
| Active ingredient | 10.0 | 5.0 |
| Lactose Hydrous, Impalpable powder USP | 772.0 | 777.0 |
| Sodium Lauryl Sulfate | 20.0 | 20.0 |
| Polyvinylpyrrolidone | 40.0 | 40.0 |
| Corn Starch, Food Grade | 150.0 | 150.0 |
| Magnesium Stearate | 8.0 | 8.0 |
| | 1000 mg | 1000 mg |

Formulation 5

| Intramuscular or Subcutaneous Oil Injection | mg/ml |
| --- | --- |
| Active ingredient | 10 -50 |
| Aluminum Monostearate, USP | 20.0 |
| Sesame Oil, Heat Treated, USP gs ad | 1.0 ml |

Formulation 6

| Topical Cream | Per kg. |
| --- | --- |
| Active ingredient | 10 g. - 100 g. |
| Stearic acid | 60 g. |
| Propylene Glycol Monostearate | 100 g. |
| Isopropyl Myristate | 80 g. |
| Polyoxyethylene (20) Sorbitan Monopalmitate | 60 g. |
| Sorbitan Solution | 20 g. |
| Buffers, Sufficient | — |
| Preservatives, Sufficient | — |
| Purified Water to make | 1.0 kg. |

Add the stearic acid, propylene glycol monostearate, isopropyl myristate and polyoxyethylene (20) sorbitan monopalmitate to a suitable mixing vessel. Heat to 80° C. to melt. Mix.

Formulations 7 to 9 illustrate compositions preserved with a compound of the formula I:

Formulation 7

| Lotion | mg/ml |
| --- | --- |
| Betamethasone Valerate | 1.22 |
| Preservative (compound of formula I or salt thereof) | 1.00 |
| Mineral Oil, USP | 19.50 |
| Diethylene Glycol Monostearate S.E. | 6.50 |
| Cetostearyl Alcohol | 6.50 |
| Lanbritol Wax | 9.30 |
| Glycerin, USP | 50.00 |
| Isopropanol | 65.00 |
| Citric Acid | 0.08 |
| Purified Water, USP, to make | 1.00 ml |

Formulation 8

| Intramuscular or Intravenous solution | mg/ml |
| --- | --- |
| Gentamicin (charged as sulfate) | 40.0 |
| Sodium Bisulfite, USP | 3.2 |
| Disodium Edetate, USP | 0.1 |
| Preservative (compound of formula I or salt thereof) | 1-3 |
| Water for Injection qs ad | 1.0 ml |

Formulation 9

| Aerosol Concentrate | mg/g |
| --- | --- |
| Megalomicin A Phosphate | 20.0 |
| Preservative (compound of formula I or salt thereof) | 1.0 |
| Liquid Absorption Base | 90.0 |
| Stearic Acid | 25.0 |
| Glyceryl Monostearate | 25.0 |
| Isopropyl Myristate | 50.0 |
| Glycerol, USP | 100.0 |
| Alcohol SD 40 | 80.0 |
| Triethanolamine | 10.0 |
| Purified Water, USP, to make | 1.0 g. |

This composition is packaged into an aerosol container with standard polyfluoroalkane propellant mixtures.

I claim:

1. A method for treating susceptible microbial infections, selected from the group consisting of bacterial, fungal and protozoal infections, which comprises administering to an animal species so infected an antimicrobially effective quantity of a compound represented by the formula:

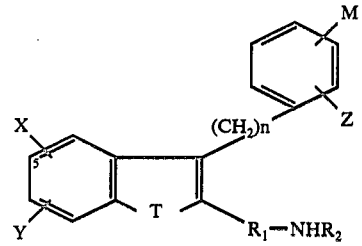

wherein $n$ is 0 or 1; $R_2$ is hydrogen, or amino lower alkylene having 1 to 3 carbon atoms; $R_1$ is carbonyl or lower alkylene having 1 to 3 carbon atoms with the provisio that when $R_2$ is hydrogen, $R_1$ is lower alkylene; T is S; X is halogen, nitro, or trifluoromethyl; Y is hydrogen, halogen, methyl or trifluoromethyl; M is hydrogen, halogen or methyl with the provisio that when X is nitro, M is halogen; Z is hydrogen, halogen, nitro or methyl; or the acid addition salts thereof.

2. The method according to claim 1 wherein $n$ is 0.
3. The method according to claim 1 wherein $R_2$ is hydrogen.
4. The method according to claim 1 wherein $R_1$ is methylene.